(12) United States Patent
Stoller et al.

(10) Patent No.: US 9,864,094 B2
(45) Date of Patent: Jan. 9, 2018

(54) SYSTEM FOR SOIL MOISTURE MONITORING

(71) Applicant: THE CLIMATE CORPORATION, San Francisco, CA (US)

(72) Inventors: Jason Stoller, Morton, IL (US); Troy Plattner, Goodfield, IL (US)

(73) Assignee: The Climate Corporation, San Francisco, CA (US)

( * ) Notice: Subject to any disclaimer, the term of this patent is extended or adjusted under 35 U.S.C. 154(b) by 127 days.

(21) Appl. No.: 14/891,770

(22) PCT Filed: May 19, 2014

(86) PCT No.: PCT/US2014/038677
§ 371 (c)(1),
(2) Date: Nov. 17, 2015

(87) PCT Pub. No.: WO2014/186810
PCT Pub. Date: Nov. 20, 2014

(65) Prior Publication Data
US 2016/0116632 A1    Apr. 28, 2016

Related U.S. Application Data

(60) Provisional application No. 61/824,975, filed on May 17, 2013.

(51) Int. Cl.
*G01N 21/00*        (2006.01)
*G01V 8/10*         (2006.01)
(Continued)

(52) U.S. Cl.
CPC ............. *G01V 8/10* (2013.01); *A01B 79/005* (2013.01); *G01N 33/24* (2013.01); *G01N 33/246* (2013.01);
(Continued)

(58) Field of Classification Search
CPC .......... G01V 9/02; G01V 3/12; A01B 79/005; G01N 2033/245; A01C 21/007; G01J 3/28
See application file for complete search history.

(56) References Cited

U.S. PATENT DOCUMENTS 4,266,878 A    5/1981 Auer
4,310,758 A    1/1982 Peterson
(Continued)

FOREIGN PATENT DOCUMENTS

WO    WO 91/04484 A1    4/1991
WO    2012129442 A3     9/2012
(Continued)

OTHER PUBLICATIONS

Visible-NIR Hyperspectral Imagery for Discrimination Soil Types in the La Peyne Watershed (France), Developments in Soil Science, vol. 31, P. Lagacherie, A.B. McBratnew and M. Voltz (Editors), J.S. Madeira Netto, J.-M. Robberz-Masson and E. Martins (Authors), Chapter 17, pp. 219-234.
(Continued)

*Primary Examiner* — Michael A Lyons
*Assistant Examiner* — Maurice Smith
(74) *Attorney, Agent, or Firm* — Hickman Palermo Becker Bingham LLP

(57) ABSTRACT

Systems, methods and apparatus are provided for moisture measurement. In some embodiments, a reflectance measurement is corrected based on a soil characteristic map. In other embodiments, a first reflectance measurement at a first depth is corrected based on a second reflectance measurement at a second depth.

12 Claims, 13 Drawing Sheets

(51) Int. Cl.
*A01B 79/00* (2006.01)
*G01N 33/24* (2006.01)
*G01V 11/00* (2006.01)
*G01V 3/12* (2006.01)
*A01C 21/00* (2006.01)

(52) U.S. Cl.
CPC .......... *G01V 11/002* (2013.01); *A01C 21/007* (2013.01); *G01N 2033/245* (2013.01); *G01V 3/12* (2013.01)

(56) References Cited

U.S. PATENT DOCUMENTS

| | | | |
|---|---|---|---|
| 5,038,040 A * | 8/1991 | Funk | G01N 21/3563 250/339.02 |
| 5,524,560 A | 6/1996 | Carter | |
| 5,739,536 A | 4/1998 | Bucholtz et al. | |
| 5,789,741 A | 8/1998 | Kinter et al. | |
| 5,841,282 A * | 11/1998 | Christy | A01B 79/005 111/118 |
| 6,041,582 A * | 3/2000 | Tiede | A01B 79/005 56/10.2 A |
| 6,356,830 B1 | 3/2002 | Adamchuck et al. | |
| 6,853,937 B2 * | 2/2005 | Shibusawa | A01B 79/005 250/253 |
| 8,204,689 B2 | 6/2012 | Christy et al. | |
| 8,935,986 B2 | 1/2015 | Blomme et al. | |
| 2003/0016029 A1 | 1/2003 | Schuler et al. | |
| 2005/0192752 A1 | 9/2005 | Rooney et al. | |
| 2009/0112475 A1 | 4/2009 | Christy et al. | |
| 2009/0322357 A1 * | 12/2009 | Beaulieu | A01G 7/00 324/692 |
| 2010/0180695 A1 | 7/2010 | Sauder et al. | |
| 2011/0102798 A1 * | 5/2011 | Holland | A01B 79/005 356/445 |
| 2011/0106451 A1 | 5/2011 | Christy et al. | |

FOREIGN PATENT DOCUMENTS

| | | |
|---|---|---|
| WO | 2012149398 A1 | 11/2012 |
| WO | 2012149415 A1 | 11/2012 |

OTHER PUBLICATIONS

Precision Farming Tools: Soil Electrical Conductivity, Publication 442-508, Robert Grisso, Mark Alley, W. G. Wysor, David Holshouser, Wade Thomason (Authors), Virginia Cooperative Extension, pp. 1-6.

Influence of Surface Soil Moisture on Spectral Reflectance of Bare Soil in the 0.4-15 μM Domain, Audrey Lesaignoux, Sophie, Fabre, Xavier Briottet, Albert Olioso (Authors), pp. 1-6.

Soil Moisture Sensor for Predicting Seed Planting Depth, R. R. Price, L.D. Gaultney (Authors), American Society of Agricultural Engineers 0001-2351/93/3606-1703, vol. 36(6), Nov.-Dec. 1993, pp. 1703-1711.

Visible-Near Infrared Reflectance Spectroscopy for Assessment of Soil Properties in a Semi-Arid Area of Turkey, A. Volkan Bilgili, H.M. van Es, F. Akbas, A. Durak, W. D. Hively (Authors), Journal of Arid Environments 74 (2010), pp. 229-238.

Soil Reflective Sensing for Determining Soil Properties in Precision Agriculture, J. A. Thomasson, R. Sui, M.S. Cox, A. Al-Rajehy (Authors), American Society of Agricultural Engineers ISSN 0001-2351, pp. 1445-1453.

Estimating Soil Spectral Properties (Visible and NIR) from Color and Roughness Field Data, Richard Escadafal, Alfredo Huete, Donald Post (Authors), Presented at the Twenty Third International Symposium on Remote Sensing of Environment, Bangkok, Thailand, Apr. 18-25, 1990, pp. 1-11.

The Potential of Near-Infrared Reflectance Spectroscopy to Analyse Soil Chemical and Physical Charateristics, D. Cozzolino, A. Moron (Authors), Journal of Agricultural Science (2003), 140, pp. 65-71.

International Search Report PCT/US2014/038677, pp. 1-17, dated Sep. 24, 2014.

European Patent Office, "Search Report" in application No. 14797184.0-1655, dated Apr. 6, 2017, 9 pages.

European Claims in application No. 14797184.0-1655, dated Apr. 2017, 2 pages.

* cited by examiner ary planter.

SYSTEM FOR SOIL MOISTURE MONITORING

BACKGROUND

In recent years, increased input costs and an increased interest in precision agriculture practices have led to the development of in-field moisture measurement. However, existing systems generate moisture estimates that change with variables other than true moisture measurement. Thus there is a need in the art for improved systems, methods and apparatus for soil moisture monitoring.

DESCRIPTION

Soil Monitoring System

Figure 1:
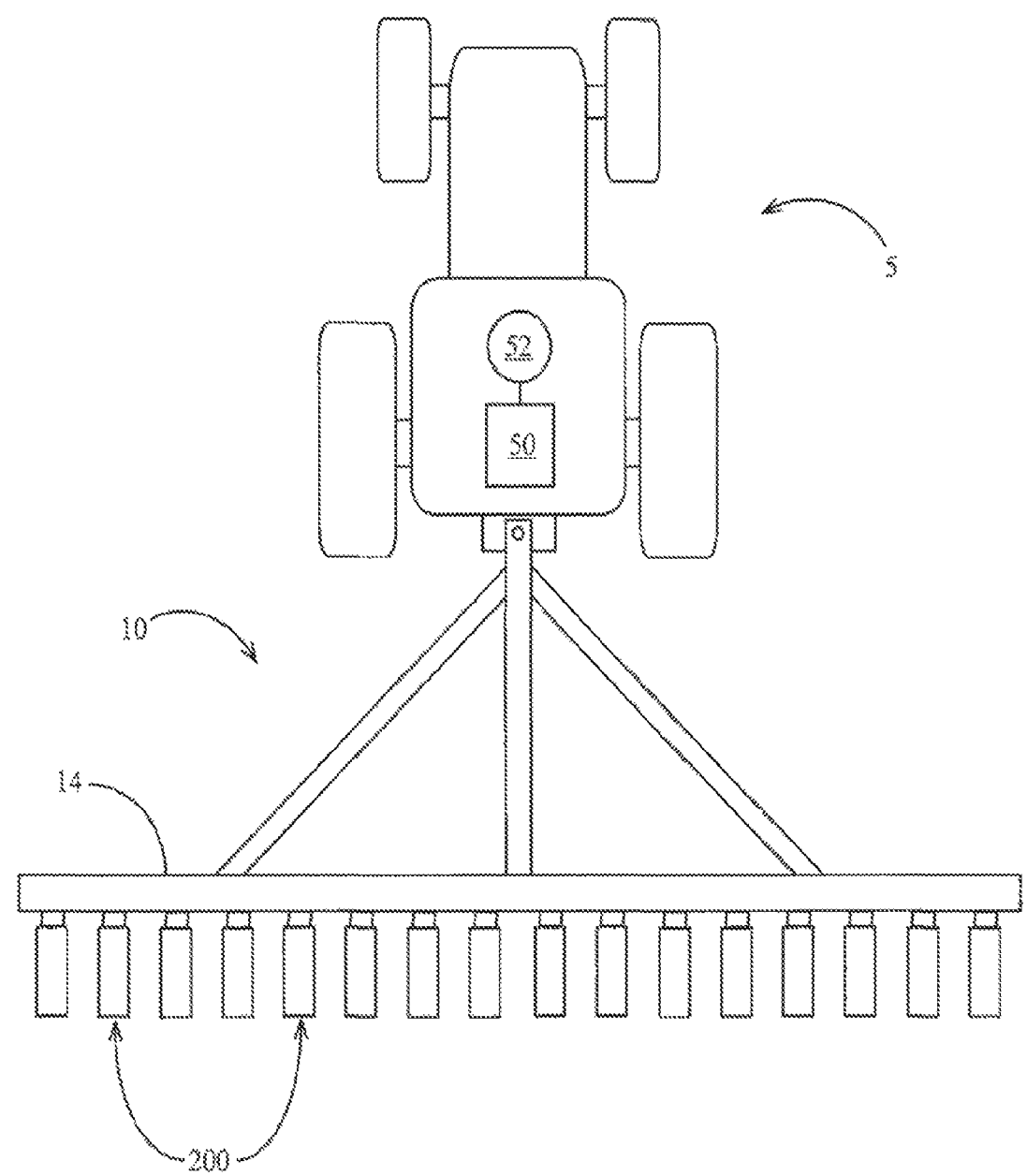
FIG. 1 is a top view of an embodiment agricultural planter.

Referring now to the drawings, wherein like reference numerals designate identical or corresponding parts throughout the several views, FIG. 1 illustrates a tractor 5 drawing an agricultural implement, e.g., a planter 10, comprising a toolbar 14 operatively supporting multiple row units 200. An implement monitor 50 preferably including a central processing unit ("CPU"), memory and graphical user interface ("GUI") (e.g., a touch-screen interface) is preferably located in the cab of the tractor 5. A global positioning system ("GPS") receiver 52 is preferably mounted to the tractor 5.

Figure 2:
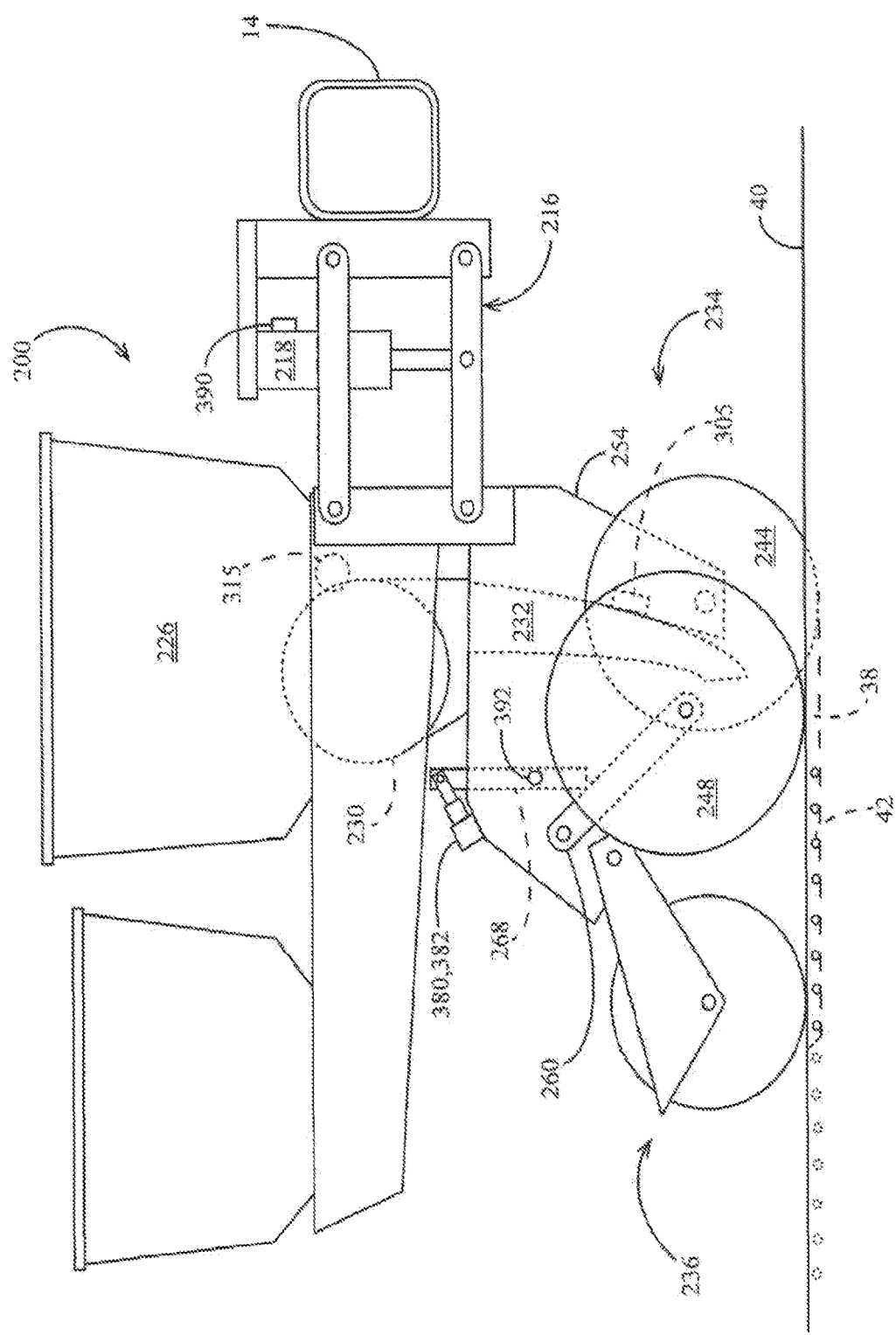
FIG. 2 is a side elevation view of an embodiment of a planter row unit.

Turning to FIG. 2, an embodiment is illustrated in which the row unit 200 is a planter row unit. The row unit 200 is preferably pivotally connected to the toolbar 14 by a parallel linkage 216. An actuator 218 is preferably disposed to apply lift and/or downforce on the row unit 200. A solenoid valve 390 is preferably in fluid communication with the actuator 218 for modifying the lift and/or downforce applied by the actuator. An opening system 234 preferably includes two opening discs 244 rollingly mounted to a downwardly-extending shank 254 and disposed to open a v-shaped trench 38 in the soil 40. A pair of gauge wheels 248 is pivotally supported by a pair of corresponding gauge wheel arms 260; the height of the gauge wheels 248 relative to the opener discs 244 sets the depth of the trench 38. A depth adjustment rocker 268 limits the upward travel of the gauge wheel arms 260 and thus the upward travel of the gauge wheels 248. A depth adjustment actuator 380 is preferably configured to modify a position of the depth adjustment rocker 268 and thus the height of the gauge wheels 248. The actuator 380 is preferably a linear actuator mounted to the row unit 200 and pivotally coupled to an upper end of the rocker 268. In some embodiments the depth adjustment actuator 380 comprises a device such as that disclosed in International Patent Application No. PCT/US2012/035585, the disclosure of which is hereby incorporated herein by reference. An encoder 382 is preferably configured to generate a signal related to the linear extension of the actuator 380; it should be appreciated that the linear extension of the actuator 380 is related to the depth of the trench 38 when the gauge wheel arms 260 are in contact with the rocker 268. A downforce sensor 392 is preferably configured to generate a signal related to the amount of force imposed by the gauge wheels 248 on the soil 40; in some embodiments the downforce sensor 392 comprises an instrumented pin about which the rocker 268 is pivotally coupled to the row unit 200, such as hose instrumented pins disclosed in Applicant's co-pending U.S. patent application Ser. No. 12/522,253 (Pub. No. US2010/0180695), the disclosure of which is hereby incorporated herein by reference.

Continuing to refer to FIG. 2, a seed meter 230 such as that disclosed in Applicant's co-pending International Patent Application No. PCT/US2012/030192, the disclosure of which is hereby incorporated herein by reference, is preferably disposed to deposit seeds 42 from a hopper 226 into the trench 38, e.g., through a seed tube 232 disposed to guide the seeds toward the trench. In some embodiments, the meter is powered by an electric drive 315 configured to drive a seed disc within the seed meter. In other embodiments, the drive 315 may comprise a hydraulic drive configured to drive the seed disc. A seed sensor 305 (e.g., an optical or electromagnetic seed sensor configured to generate a signal indicating passage of a seed) is preferably mounted to the seed tube 232 and disposed to send light or electromagnetic waves across the path of seeds 42. A closing system 236 including one or more closing wheels is pivotally coupled to the row unit 200 and configured to close the trench 38.

Figure 3:
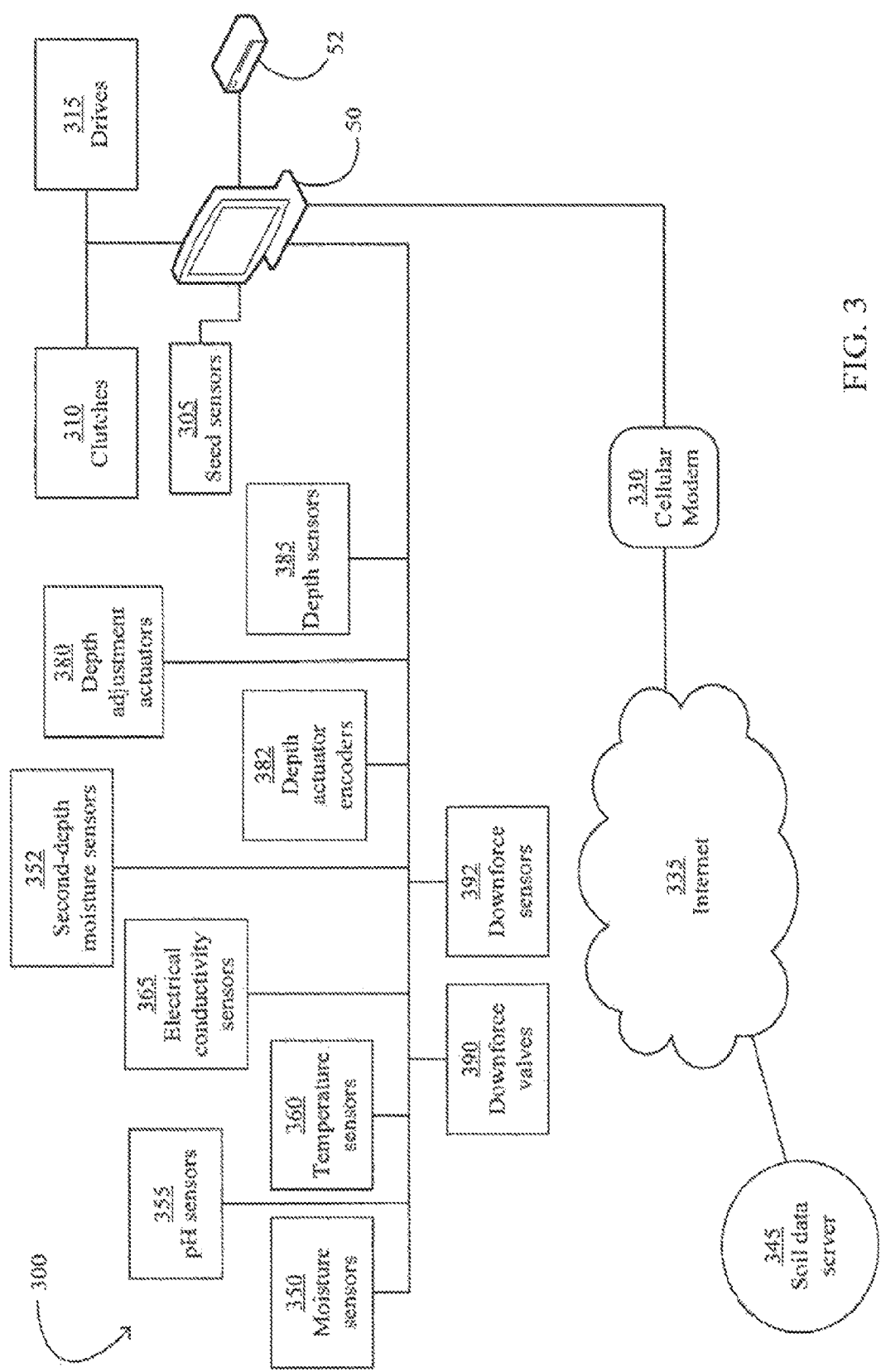
FIG. 3 schematically illustrates an embodiment of a soil monitoring system.

Turning to FIG. 3, a depth control and soil monitoring system 300 is schematically illustrated. The monitor 50 is preferably in electrical communication with components associated with each row unit 200 including the drives 315, the seed sensors 305, the GPS receiver 52, the downforce sensors 392, the valves 390, the depth adjustment actuators 380, the depth actuator encoders 382 (and in some embodiments actual depth sensors 385 such as those described in applicant's co-pending U.S. Provisional Patent Application No. 61/718,073, incorporated by reference herein), and the solenoid valves 390. In some embodiments, particularly those in which each seed meter 230 is not driven by an individual drive 315, the monitor 50 is also preferably in electrical communication with clutches 310 configured to selectively operably couple the seed meter 230 to the drive 315.

Figure 4:
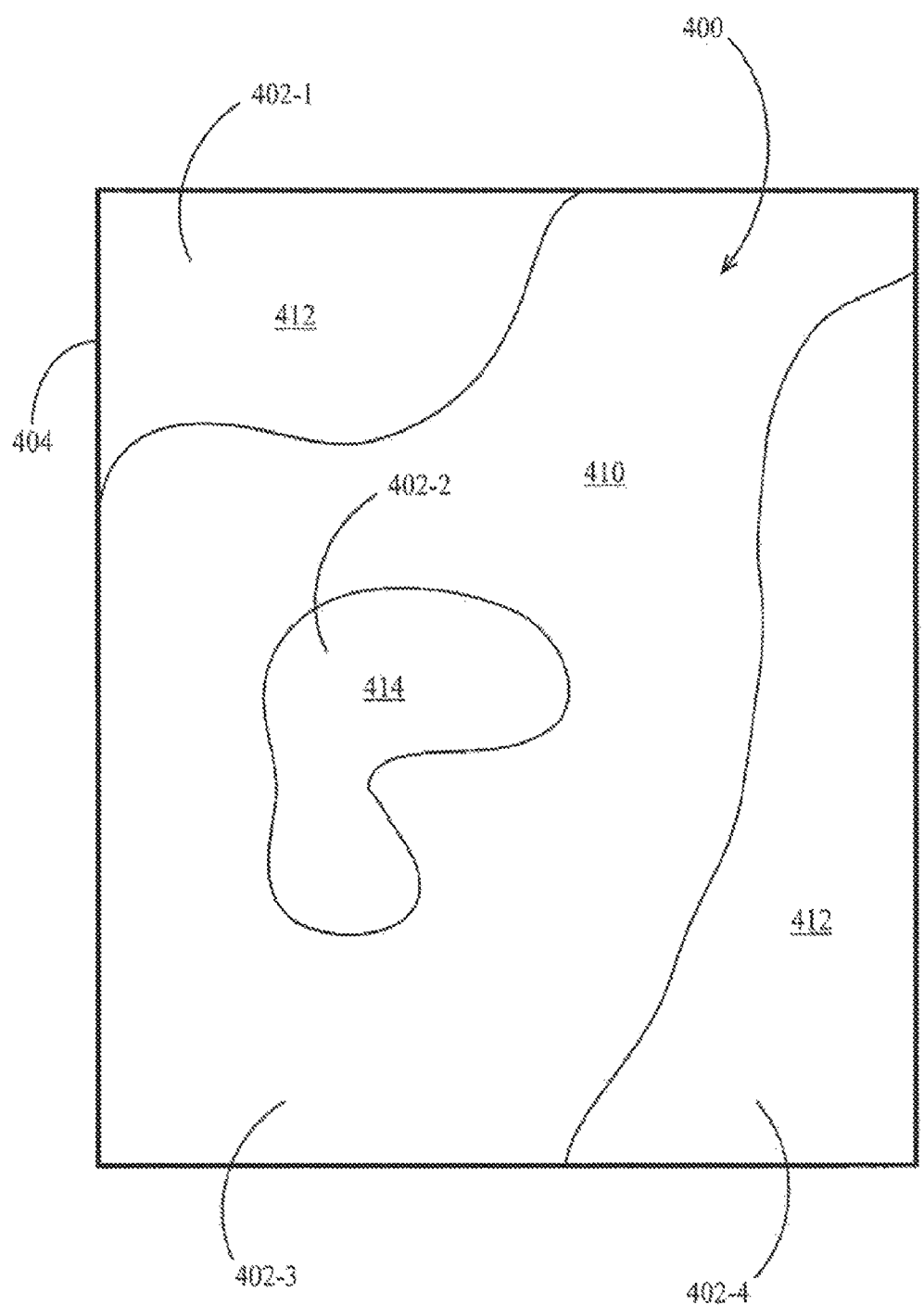
FIG. 4 illustrates an embodiment of a soil characteristic map.

Continuing to refer to FIG. 3, the monitor 50 is preferably in electrical communication with a cellular modem 330 or other component configured to place the monitor 50 in data communication with the Internet, indicated by reference numeral 335. Via the Internet connection, the monitor 50 preferably receives data from a soil data server 345. The soil data server 345 preferably includes soil map files (e.g., shape files) associating soil types (or other soil characteristics) with GPS locations. In some embodiments, soil map files are stored in the memory of the monitor 50. An exemplary soil map 400 is illustrated in FIG. 4. The soil map 400 comprises a soil type map in which soil type polygons 402-1, 402-2, 402-3, 402-4 within a field boundary 404 are associated with soil types 412, 414, 410, 412 respectively.

Returning to FIG. 3, the monitor 50 is also preferably in electrical communication with one or more temperature sensors 360 mounted to the planter 10 and configured to generate a signal related to the temperature of soil being worked by the planter row units 200. In some embodiments one or more of the temperature sensors 360 comprise thermocouples disposed to engage the soil as disclosed in Applicant's co-pending U.S. provisional patent application No. 61/783,591 ("the '591 application"), the disclosure of which is incorporated herein in its entirety by reference; in such embodiments the temperature sensors 360 preferably engage the soil at the bottom of the trench 38. In other embodiments, one or more of the temperature sensors 360 may comprise a sensor disposed and configured to measure the temperature of the soil without contacting the soil as disclosed in International Patent Application No. PCT/US2012/035563, the disclosure of which is hereby incorporated herein in its entirety by reference.

Referring to FIG. 3, the monitor 50 is preferably in electrical communication with one or more moisture sensors 350 mounted to the planter 10 and configured to generate a signal related to the temperature of soil being worked by the planter row units 200. In some embodiments, the moisture sensor 350 comprises a reflectance sensor such as that disclosed in U.S. Pat. No. 8,204,689 ("the '689 application"), hereby incorporated herein by reference. In such embodiments, the moisture sensor 350 is preferably mounted to the shank 254 of the row unit 200 and disposed to measure the soil moisture at the bottom of the trench 38, preferably at a position longitudinally forward of the seed tube 232. The monitor 50 is preferably in electrical communication with one or more second-depth moisture sensors 352. The second-depth moisture sensor 352 preferably comprises a reflectance sensor such as that disclosed in the '689 application, disposed to measure soil moisture at a depth at which consistent moisture reading is expected. In some embodiments the second-depth moisture sensor 352 is disposed to measure soil moisture at a greater depth than used for planting, such as between 3 and 6 inches and preferably approximately 4 inches below the soil surface. In other embodiments the second-depth moisture sensor 352 is disposed to measure soil moisture at a lesser depth than used for planting, such as between 0.25 inch and 1 inch and preferably approximately 0.5 inch below the soil surface. The second-depth moisture sensor 352 is preferably disposed to open a trench laterally offset from the trenches 38 opened by the row units 200.

Figure 13:
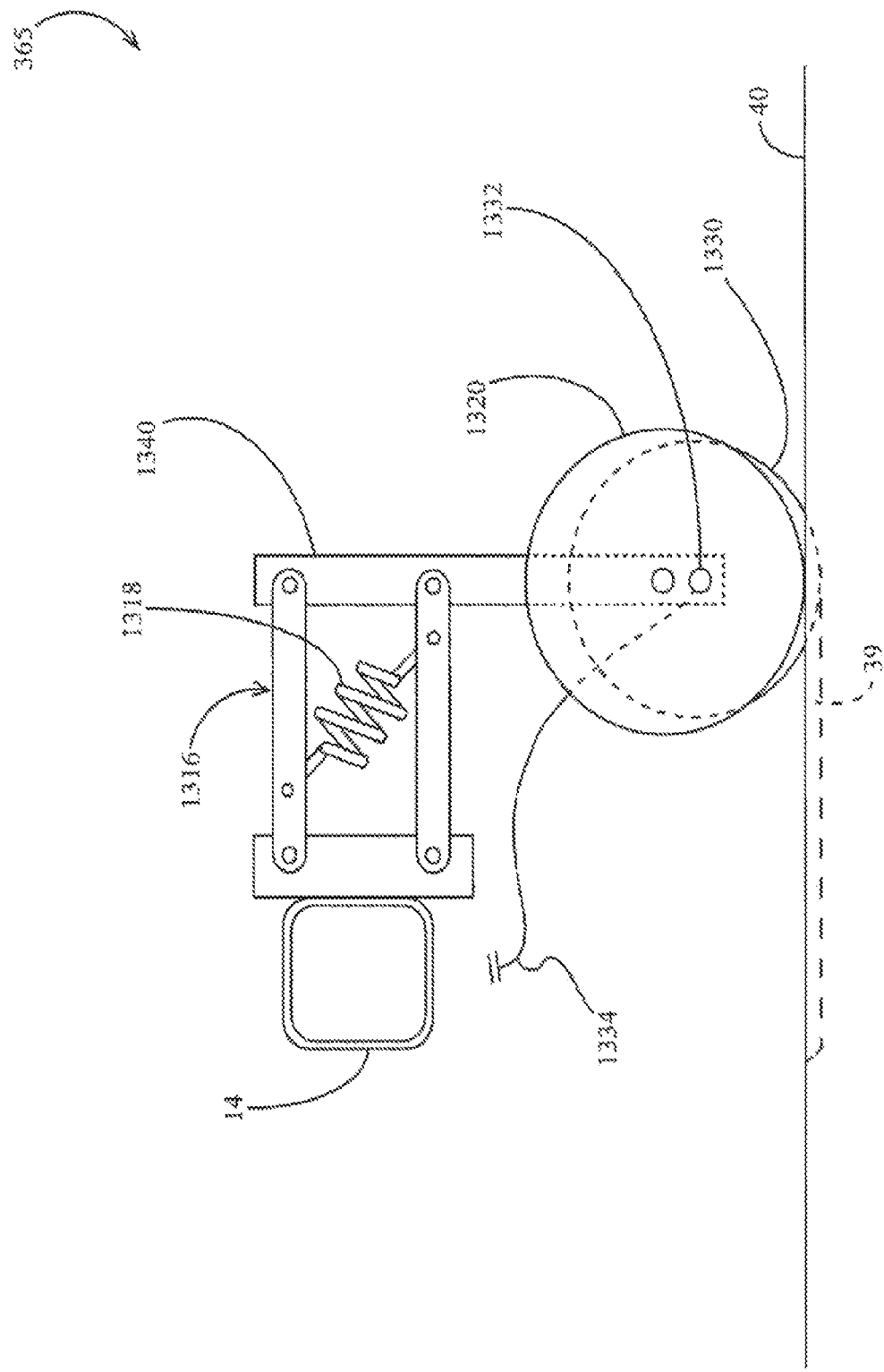
FIG. 13 illustrates an embodiment of an electrical conductivity sensor.

Referring to FIG. 3, the monitor 50 is preferably in electrical communication with one or more electrical conductivity sensors 365. The electrical conductivity sensor 365 preferably comprises one or more electrodes disposed to cut into the soil surface such as the sensors disclosed in U.S. Pat. Nos. 5,841,282 and 5,524,560, both of which are hereby incorporated herein in their entirety by reference. Another embodiment of the electrical conductivity sensor 365 is illustrated in FIG. 13. The electrical conductivity sensor 365 preferably includes one or more conductive opener discs 1330 disposed to cut into the soil. The discs 1330 are preferably rollingly mounted to a support 1340 about a bearing 1332. The bearing 1332 is preferably in electrical contact with the opener discs 1330 but electrically isolated from the support 1340, e.g., by being mounted within an insulating material. The bearing 1332 is preferably in electrical communication with the monitor 50 via an electrical lead 1334. One or more gauge wheels 1320 are preferably rollingly mounted to the support 1340 and disposed to ride along the soil surface 40, setting the depth of a trench 39 opened by the opener discs 1330. The support 1340 is preferably mounted to the toolbar 14 by a parallel arm arrangement 1316. The opener discs 1330 are preferably biased into engagement with the soil by a spring 1318 mounted to the parallel arm arrangement 1316. In still another embodiment of the electrical conductivity sensor 365, the opener discs 244 of the row unit 200 are rollingly mounted to the shank 254 by a shaft; the shaft is preferably in electrical contact with the opener discs 244 but electrically isolated from the shank 254, e.g., by being mounted within an insulating material. The shaft is preferably in electrical communication with the monitor 50.

Referring to FIG. 3, the monitor 50 is preferably in electrical communication with one or more pH sensors 355. In some embodiments the pH sensor 355 is drawn by a tractor or by another implement (e.g., a tillage implement) such that data is stored in the monitor 50 for later use. In some such embodiments, the pH sensor 355 is similar to that disclosed in U.S. Pat. No. 6,356,830. In some embodiments, the pH sensor 355 is mounted to the toolbar 14, preferably at a position laterally offset from the row units 200.

Moisture Measurement Methods

Figure 5:
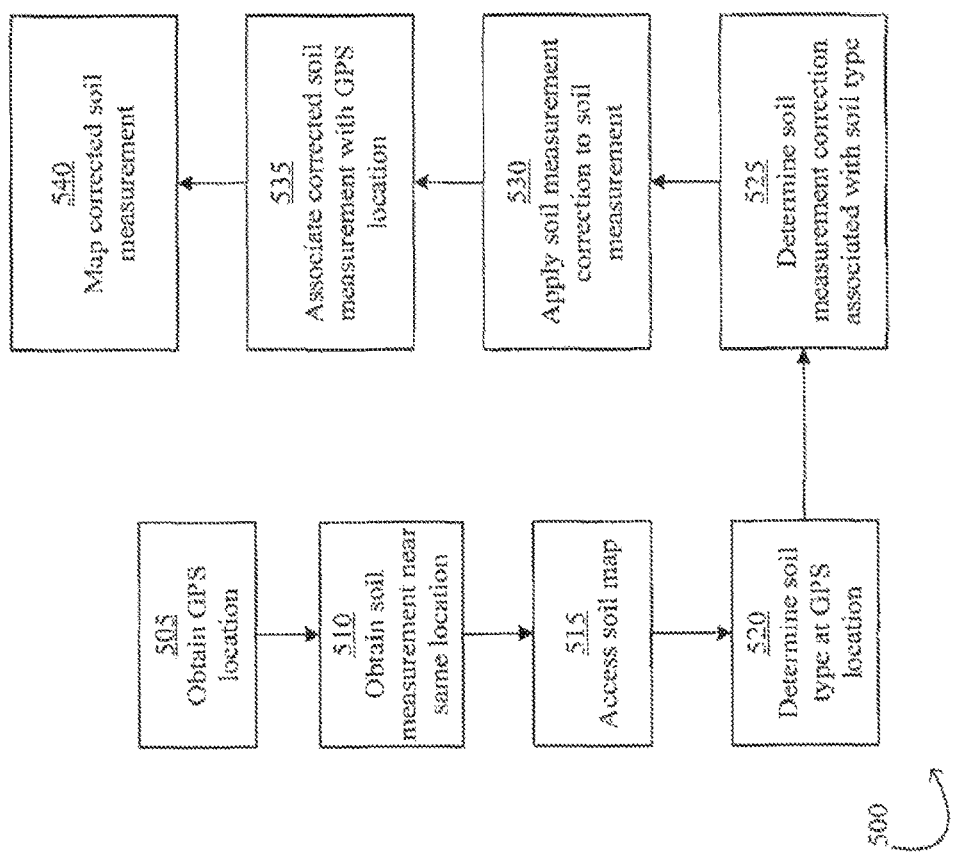
FIG. 5 illustrates an embodiment of a process for correcting a soil measurement based on soil type.

Turning to FIG. 5, a process 500 for correcting a soil measurement with a soil map is illustrated. At step 505, the monitor 50 preferably determines the GPS location of the planter 10. At step 510, the monitor 50 preferably obtains a soil measurement near the obtained GPS location. At step 515, the monitor 50 preferably accesses a soil map such as the soil type map 400 described herein and illustrated in FIG. 4. At step 520, the monitor 50 preferably determines a soil characteristic such as a soil type at the GPS location, e.g., by determining the soil type associated with the GPS location within the soil type map 400. At step 525, the monitor 50 preferably determines a soil measurement correction associated with the soil characteristic (e.g., soil type) at the GPS location. For example, the monitor 50 may have a table stored in memory including multiple soil measurement corrections, each associated with a soil characteristic (e.g., soil type). At step 530, the monitor 50 preferably applies the soil measurement correction to the soil measurement, e.g., by adding the soil measurement correction to the soil measurement. At step 535, the monitor 50 preferably associates the corrected soil measurement with the GPS location, e.g., by storing the corrected soil measurement in a data array along with the GPS location. At step 540, the monitor 50 preferably displays a map of the corrected soil measurement.

Figure 6:
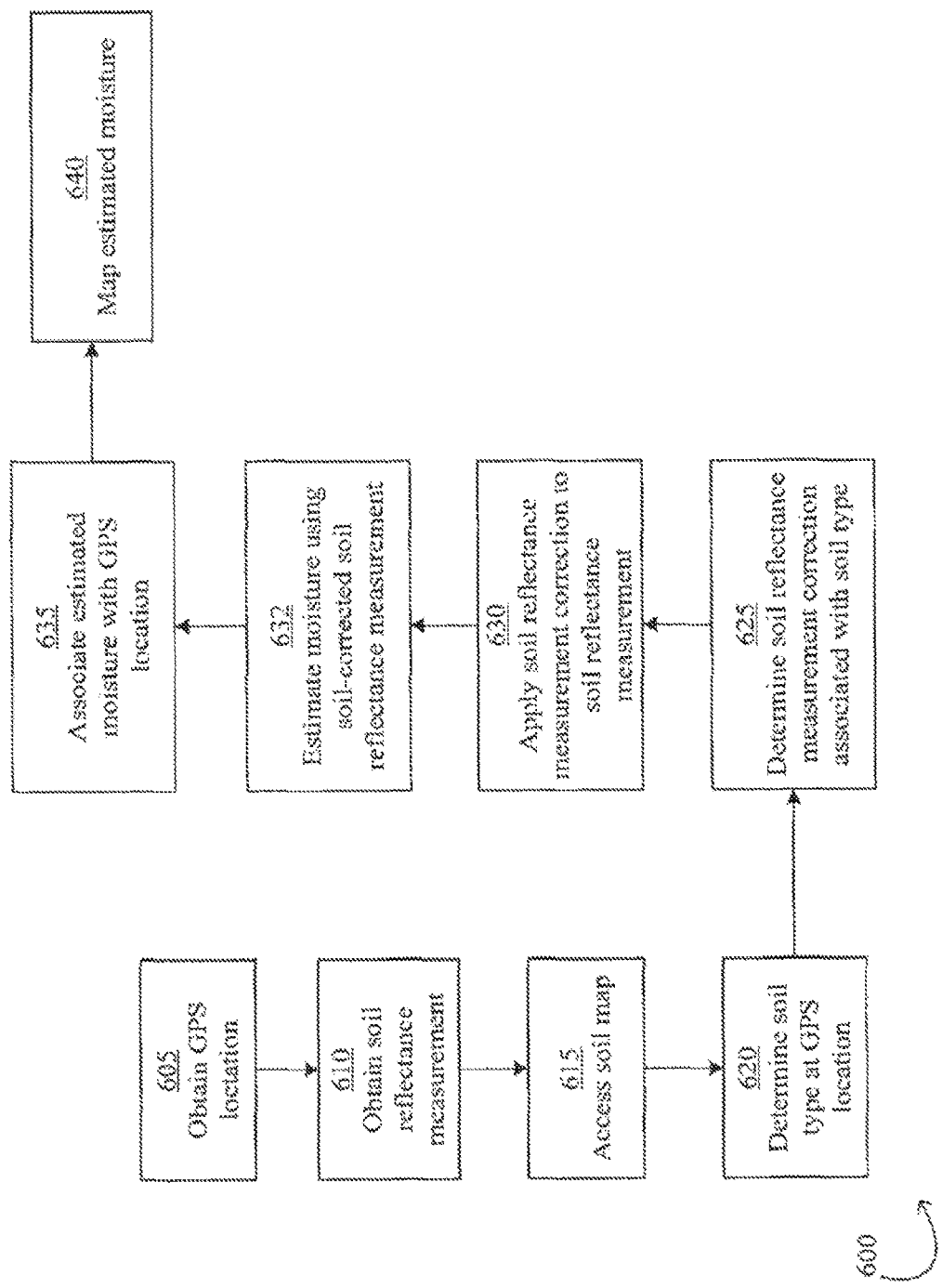
FIG. 6 illustrates an embodiment of a process for correcting a soil reflectance measurement based on soil type.

Turning to FIG. 6, a process 600 for correcting a reflectance-based moisture measurement with a soil map is illustrated. At step 605, the monitor 50 preferably determines the GPS location of the planter 10. At step 610, the monitor 50 preferably obtains a soil reflectance measurement (i.e., a reflectance value, measured as a percentage) near the obtained GPS location using the moisture sensor 350. At step 615, the monitor 50 preferably accesses a soil map such as the soil type map 400 described herein and illustrated in FIG. 4. At step 620, the monitor 50 preferably determines a soil characteristic such as a soil type at the GPS location, e.g., by determining the soil type associated with the GPS location within the soil type map 400. At step 625, the monitor 50 preferably determines a soil reflectance measurement correction associated with the soil characteristic (e.g., soil type) at the GPS location. For example, the monitor 50 may have a table stored in memory including multiple soil reflectance measurement corrections, each associated with a soil characteristic (e.g., soil type). In one embodiment, the monitor 50 determines a correction of 7% relative reflectance for reflectance values measured in soil classified as clay; a correction of −7% relative reflectance for reflectance values measured in soil classified as sand, sandy loam, or loamy sand; and a correction of 8% relative reflectance for reflectance values measured in soil classified as silt or silty loam.

Continuing to refer to FIG. 6, at step 630 the monitor 50 preferably applies the soil reflectance measurement correction to the soil measurement, e.g., by adding the soil reflectance measurement correction to the soil reflectance measurement. At step 632, the monitor 50 preferably estimates a soil measurement (e.g., soil moisture) using the corrected soil reflectance measurement. In one such embodiment, the soil reflectance measurement is made at a wavelength of about 1600 nanometers and the monitor 50 estimates the soil moisture M (in percent water weight) based on the corrected soil reflectance R (measured as a percentage) using the equation:

$$M = 80 - 1.4R$$

Where: R is the relative reflectance expressed as a percentage, and
M is the soil moisture content by weight, expressed as a percentage and corresponding to the value calculated using dry sample weight Wd and wet sample weight Ww in the following equation:

$$M = \frac{W_w - W_d}{W_w} \times 100\%$$

Figure 12:
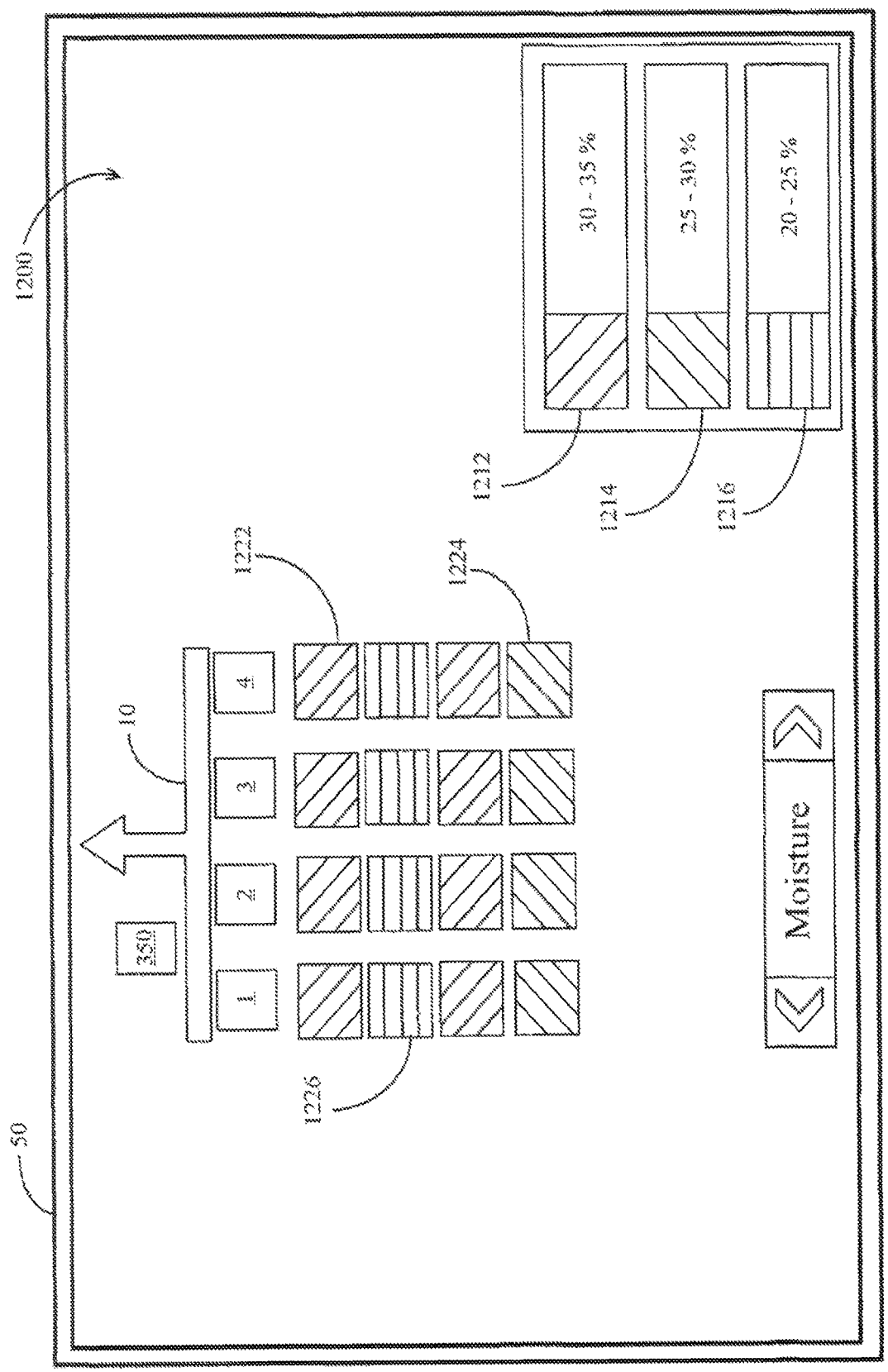
FIG. 12 illustrates an embodiment of a soil moisture map.

Continuing to refer to FIG. 6, at step 635 the monitor 50 preferably associates the estimated soil measurement (e.g., soil moisture) with the GPS location, e.g., by storing the estimated soil measurement in a data array along with the GPS location. At step 640, the monitor 50 preferably displays a map of the estimated soil measurement, as illustrated in exemplary moisture map 1200 of FIG. 12. In the embodiment of FIG. 12, a single moisture sensor 350 is mounted to the toolbar 14 such that one of the images 1224, 1224, 1226 associated with legend ranges 1212, 1214, 1216 is displayed along the entire width of the planter 10 at each longitudinal position corresponding to a corrected moisture measurement determined as described herein. In some embodiments, the monitor 50 also displays the numerical value of the corrected moisture measurement, preferably averaged over a distance (e.g., 50 feet) previously traversed by the toolbar 14.

Figure 7:
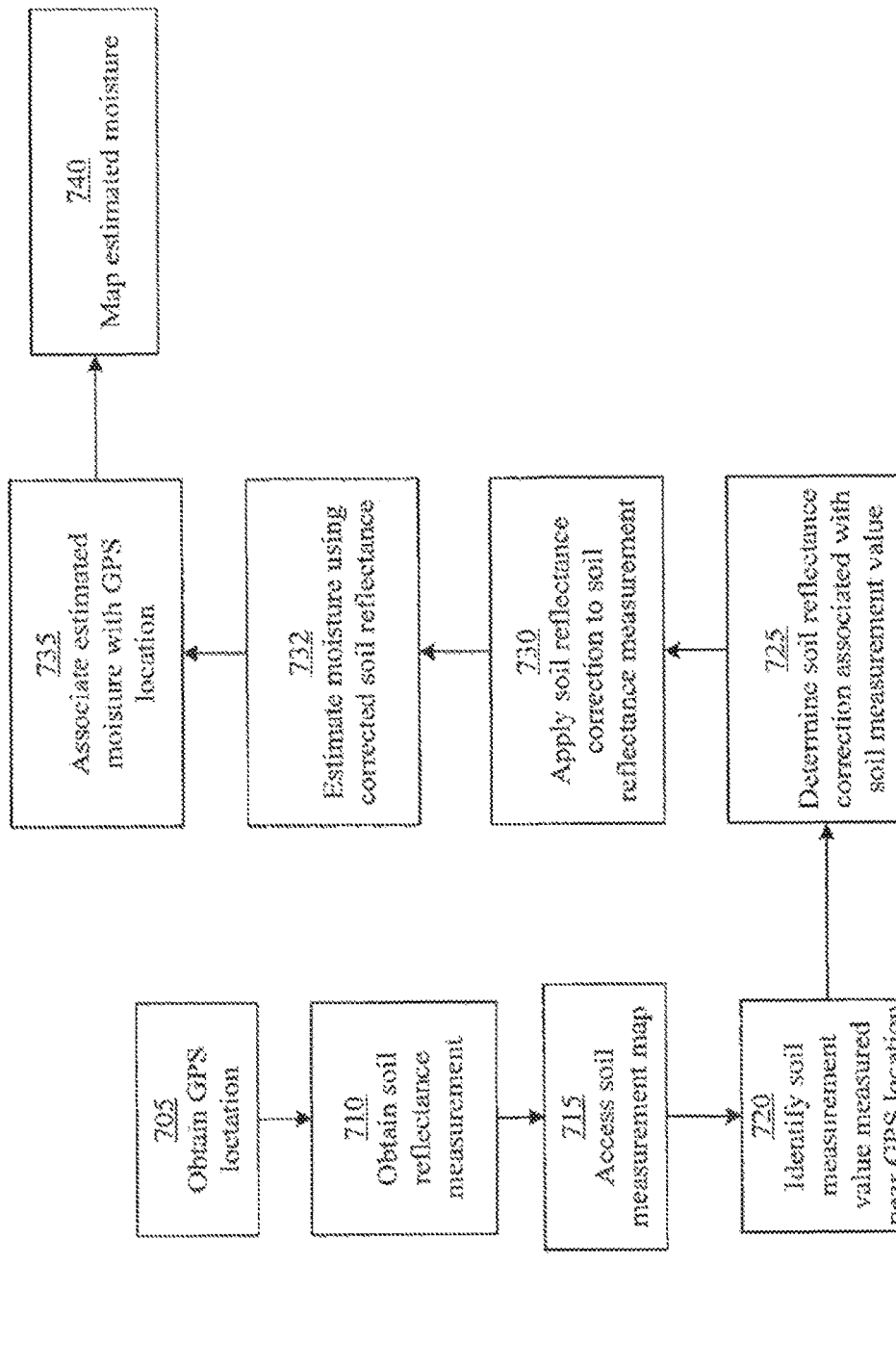
FIG. 7 illustrates an embodiment of a process for correcting a soil reflectance measurement using a soil measurement map.

Turning to FIG. 7, a process 700 for correcting a reflectance-based moisture measurement made during an in-field operation using a previously created soil measurement map is illustrated. At step 705, the monitor 50 preferably determines the GPS location of the planter 10. At step 710, the monitor 50 preferably obtains a soil reflectance measurement near the obtained GPS location using the moisture sensor 350. At step 715, the monitor 50 preferably accesses a soil measurement map. The soil measurement map preferably comprises a file associating geo-referenced locations with soil measurements made either during the planting operation or during a previous operation. Each soil measurement spatially represented in the soil measurement map may comprise an electrical conductivity measurement made using the electrical conductivity sensor 365, a pH measurement made using the pH sensor 355, a second soil reflectance measurement made at a different depth using the second-depth moisture sensor 352, or another measurement of soil content or characteristics. At step 720, the monitor 50 preferably identifies a soil measurement value associated with the GPS location in the soil measurement map; it should be appreciated that the GPS location will correspond to a region of the soil measurement map which is associated with a soil measurement value.

Continuing to refer to FIG. 7, at step 725 the monitor 50 preferably determines a soil reflectance measurement correction associated with the soil measurement associated with the GPS location. For example, the monitor 50 may have a table stored in memory including multiple soil reflectance measurement corrections, each associated with a soil measurement range. In one embodiment the soil measurement is electrical conductivity and the monitor 50 determines a correction of 7% relative reflectance for reflectance values measured in soil having an electrical conductivity greater than 10 milliSiemens per meter (10 mS/m) and a correction of −7% relative reflectance for reflectance values measured in soil having an electrical conductivity less than 2 mS/m.

Continuing to refer to FIG. 7, at step 730 the monitor 50 preferably applies the soil reflectance measurement correction to the soil reflectance measurement, e.g., by adding the soil reflectance measurement correction to the soil reflectance measurement. At step 732, the monitor 50 preferably estimates a soil measurement (e.g., soil moisture) using the corrected soil reflectance measurement; in some embodiments the step 732 is carried out as described above with respect to step 632 of process 600. At step 735, the monitor 50 preferably associates the estimated soil measurement (e.g., soil moisture) with the GPS location, e.g., by storing the estimated soil measurement in a data array along with the GPS location. At step 740, the monitor 50 preferably displays a map of the estimated soil measurement similar to that illustrated in FIG. 12.

Figure 8:
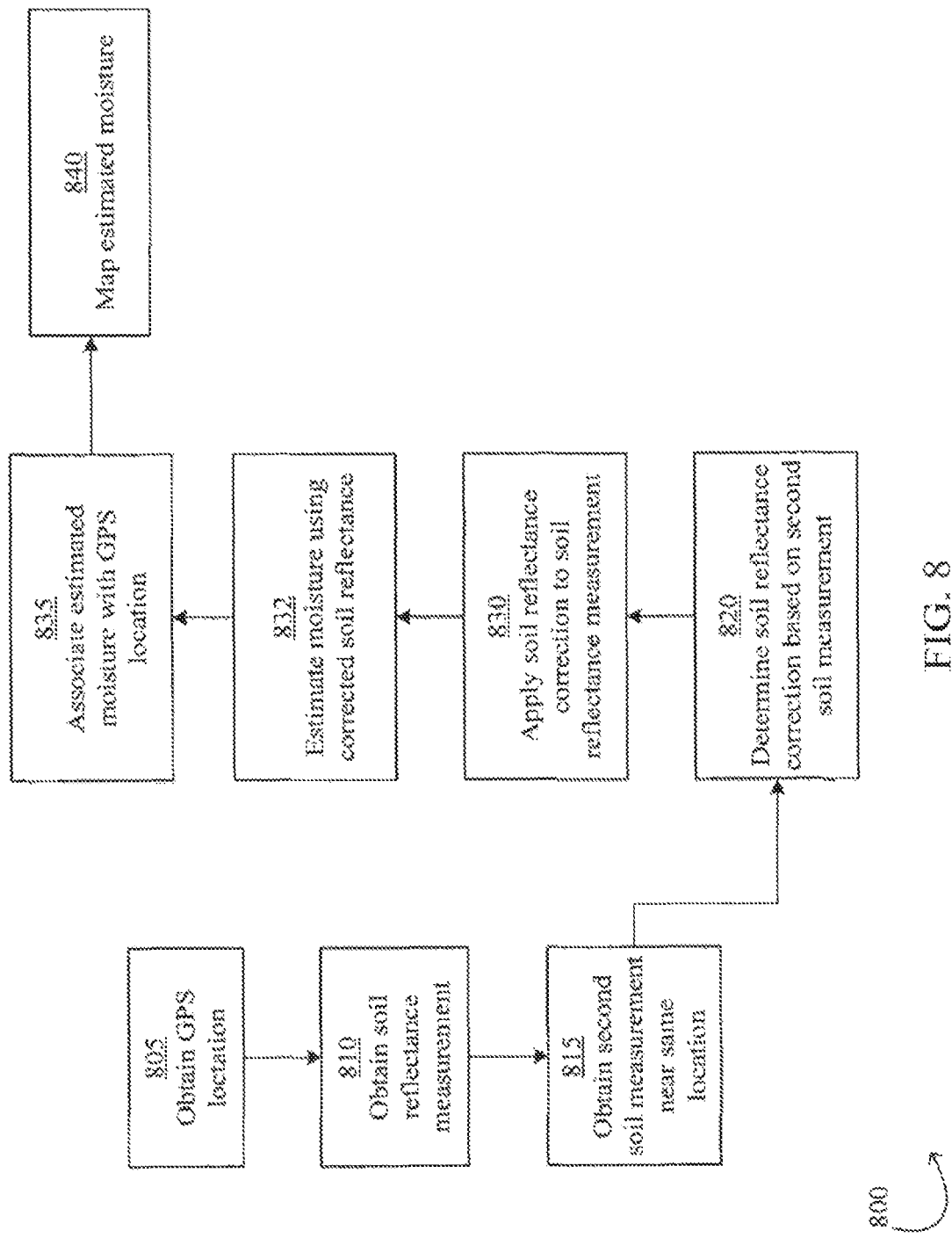
FIG. 8 illustrates an embodiment of a process for correcting a soil reflectance measurement based on a second soil characteristic measurement.

Turning to FIG. 8, a process 800 for correcting an reflectance-based moisture measurement made during an in-field operation with another soil measurement made during the same in-field operation is illustrated. At step 805, the monitor 50 preferably determines the GPS location of the planter 10. At step 810, the monitor 50 preferably obtains a soil reflectance measurement near the obtained GPS location using the moisture sensor 350. At step 815, the monitor 50 preferably obtains a second soil measurement near the obtained GPS location. The second soil measurement may comprise an electrical conductivity measurement, a pH measurement, a second soil reflectance measurement made at a different depth using the second-depth moisture sensor 352, a second soil reflectance measurement made at a different wavelength using either the second-depth moisture sensor 352 or the moisture sensor 350, or another measurement of soil content or characteristics. At step 820, the monitor 50 preferably determines a soil reflectance measurement correction associated with the second soil measurement. For example, the monitor 50 may have a table stored in memory including multiple soil reflectance measurement corrections, each associated with a soil measurement range. In one embodiment, the second soil measurement is electrical conductivity and the correction is determined as described above with respect to step 720 of the process 700. At step 830, the monitor 50 preferably applies the soil reflectance measurement correction to the soil reflectance measurement, e.g., by adding the soil reflectance measurement correction to the soil reflectance measurement. At step 832, the monitor 50 preferably estimates a soil measurement (e.g., soil moisture) using the corrected soil reflectance measurement; in some embodiments the step 832 is carried out as described above with respect to step 632 of process 600. At step 835, the monitor 50 preferably associates the estimated soil measurement (e.g., soil moisture) with the GPS location, e.g., by storing the estimated soil measurement in a data array along with the GPS location. At step 840, the monitor 50 preferably displays a map of the estimated soil measurement similar to that illustrated in FIG. 12.

Figure 9:
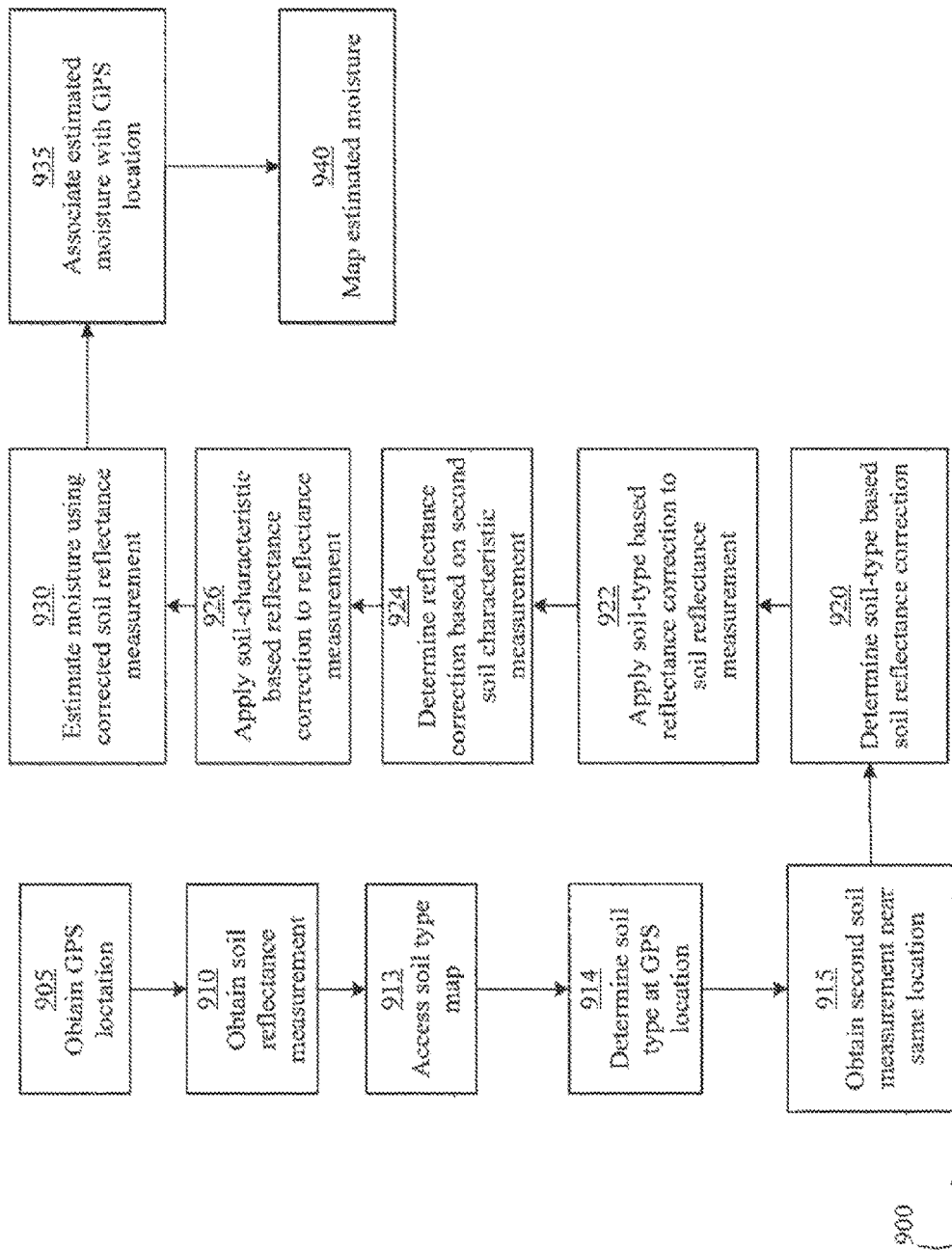
FIG. 9 illustrates an embodiment of a process for correcting a soil reflectance measurement based on a soil type and a second soil characteristic measurement.

Turning to FIG. 9, a process 900 for correcting a reflectance-based moisture measurement made during an in-field operation using a previously created soil map as well as another soil measurement made during the same in-field operation is illustrated. At step 905, the monitor 50 preferably determines the GPS location of the planter 10. At step 910, the monitor 50 preferably obtains a soil reflectance measurement near the obtained GPS location using the moisture sensor 350. At step 913, the monitor 50 preferably accesses a soil type map such as the soil type map 400 described herein and illustrated in FIG. 4. At step 914, the monitor 50 preferably determines a soil characteristic such as a soil type at the GPS location, e.g., by determining the soil type associated with the GPS location within the soil type map 400. At step 915, the monitor 50 preferably obtains a second soil measurement near the obtained GPS location. The second soil measurement may comprise an electrical conductivity measurement, a pH measurement, a second soil reflectance measurement made at a different depth using the second-depth moisture sensor 352, a second soil reflectance measurement made at a different wavelength using either the second-depth moisture sensor 352 or the moisture sensor 350, or another measurement of soil content or characteristics. At step 920, the monitor 50 preferably determines a soil reflectance measurement correction associated with the soil characteristic (e.g., soil type) at the GPS location; in some embodiments, the step 920 is carried out similarly to the step 625 of the process 600. At step 922, the monitor 50 preferably applies the soil reflectance measurement correction determined at step 920 to the soil reflectance measurement, e.g., by adding the soil reflectance measurement correction to the soil reflectance measurement. At step 924, the monitor 50 preferably determines a soil reflectance measurement correction associated with the second soil measurement. For example, the monitor 50 may have a table stored in memory including multiple soil reflectance measurement corrections, each associated with a soil measurement range. In some embodiments, the second soil measurement is electrical conductivity and the step 924 is carried out similarly to the step 720 of the process 700. At step 926, the monitor 50 preferably applies the soil reflectance measurement correction determined at step 924 to the soil reflectance measurement, e.g., by adding the soil reflectance measurement correction to the soil reflectance measurement. At step 930, the monitor 50 preferably estimates a soil measurement (e.g., soil moisture) using the soil reflectance measurement corrected at steps 922 and 926. In some embodiments, the step 930 is carried out similarly to the step 632 of the process 600. At step 935, the monitor 50 preferably associates the estimated soil measurement (e.g., soil moisture) with the GPS location, e.g., by storing the estimated soil measurement in a data array along with the GPS location. At step 940, the monitor 50 preferably displays a map of the estimated soil measurement similar to that illustrated in FIG. 12.

Figure 10:
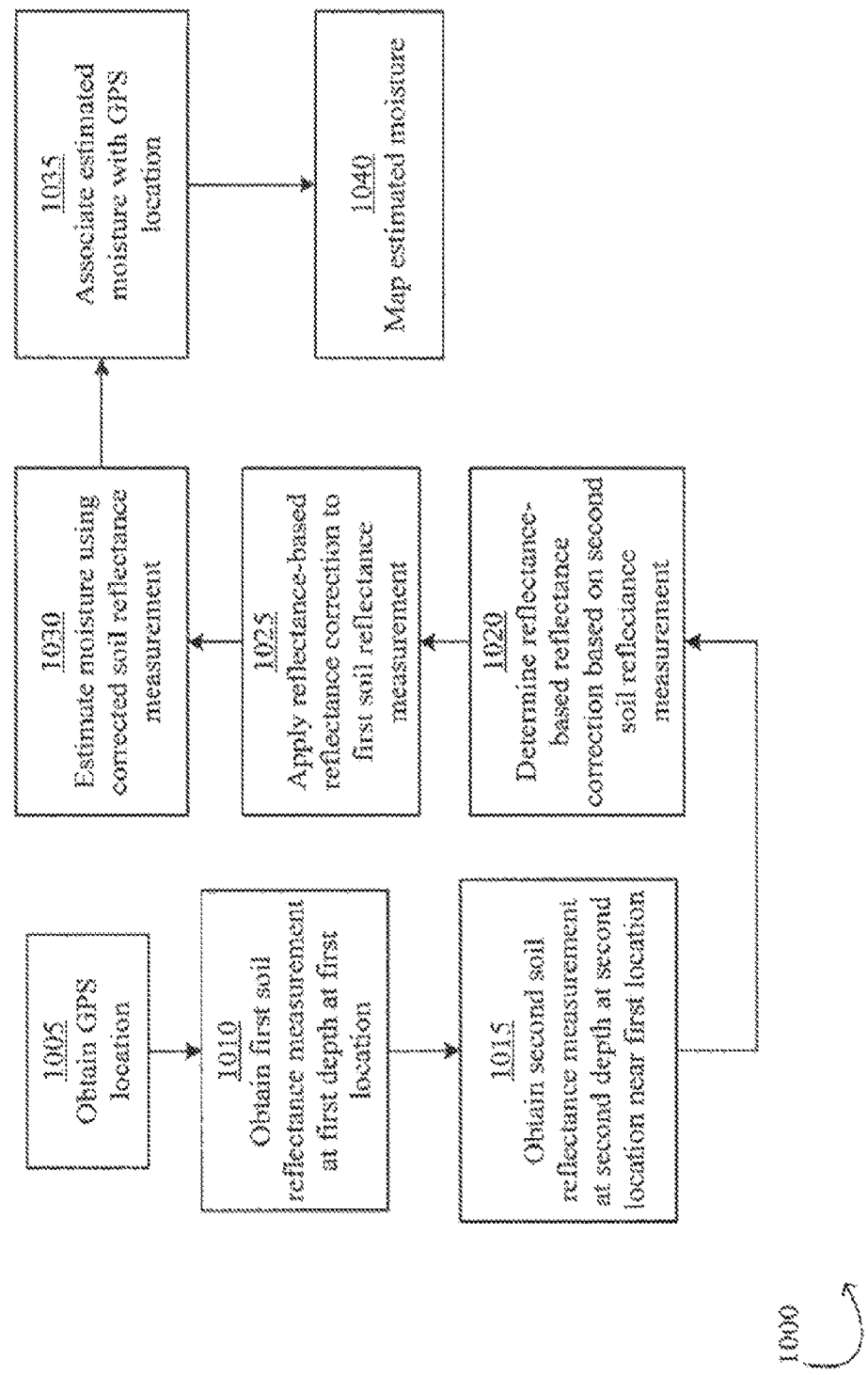
FIG. 10 illustrates an embodiment of a process for correcting a soil reflectance measurement based on a second soil reflectance measurement.

Turning to FIG. 10, a process 1000 for correcting a first reflectance-based moisture measurement made at a first depth during an in-field operation using a second reflectance-based moisture measurement made at a second depth is illustrated. At step 1005, the monitor 50 preferably determines the GPS location of the planter 10. At step 1010, the monitor 50 preferably obtains a first soil reflectance measurement near the obtained GPS location using the moisture sensor 350. The soil reflectance measurement made at step 1010 is made at a first depth; in some embodiments, the first depth is the same or approximately the same depth as the seed trench 38 opened by a row unit 16 of the planter 10. At step 1015, the monitor 50 preferably obtains a second soil reflectance measurement near the obtained GPS location at a second depth substantially different than the first depth. In some embodiments the second depth is between 3 and 6 inches and preferably approximately 4 inches. In other embodiments, the second depth is between ½ inch and 1 inch and preferably approximately 0.75 inch. The second soil reflectance measurement is preferably made using a second-depth moisture sensor 352. In some embodiments, the second soil reflectance measurement is made using a second-depth moisture sensor mounted to the planter 10 such that the second soil reflectance measurement is made during the same in-field operation as the first soil reflectance measurement. In other embodiments, the second soil reflectance measurement is made during a prior in-field operation; for example, a second-depth moisture sensor 352 may be mounted to a toolbar used for soil tillage prior to planting.

Continuing to refer to FIG. 10, at step 1020, the monitor 50 preferably determines a soil reflectance measurement correction associated with the second soil reflectance measurement obtained at step 1015. For example, the monitor 50 may have a table stored in memory including multiple soil reflectance measurement corrections, each associated with a soil reflectance measurement range. In some embodiments, the second soil reflectance measurement is carried out at a depth (e.g., 4 inches) at which consistent and high moisture is expected and the correction C is calculated using the equation:

$$C = \frac{R_a}{R_e}$$

Where: Ra is the value of the second soil reflectance measurement; and
Re is an empirically determined expected value of the second soil reflectance measurement.

In some embodiments, the monitor 50 includes values of Re stored in memory, each corresponding to a soil type; in such embodiments the monitor 50 identifies the soil type near the GPS location and selects a value of Re corresponding to the soil type.

Continuing to refer to FIG. 10, at step 1025 the monitor 50 preferably applies the soil reflectance measurement correction obtained at step 1020 to the soil reflectance measurement, e.g., by multiplying the soil reflectance measurement correction by the soil reflectance measurement. At step 1030, the monitor 50 preferably estimates a soil measurement (e.g., soil moisture) using the corrected soil reflectance measurement; in some embodiments, the step 1030 is carried out in a substantially similar to the step 632 of the process 600. At step 1035, the monitor 50 preferably associates the estimated soil measurement (e.g., soil moisture) with the GPS location, e.g., by storing the estimated soil measurement in a data array along with the GPS location. At step 1040, the monitor 50 preferably displays a map of the estimated soil measurement similar to that illustrated in FIG. 12.

Figure 11:
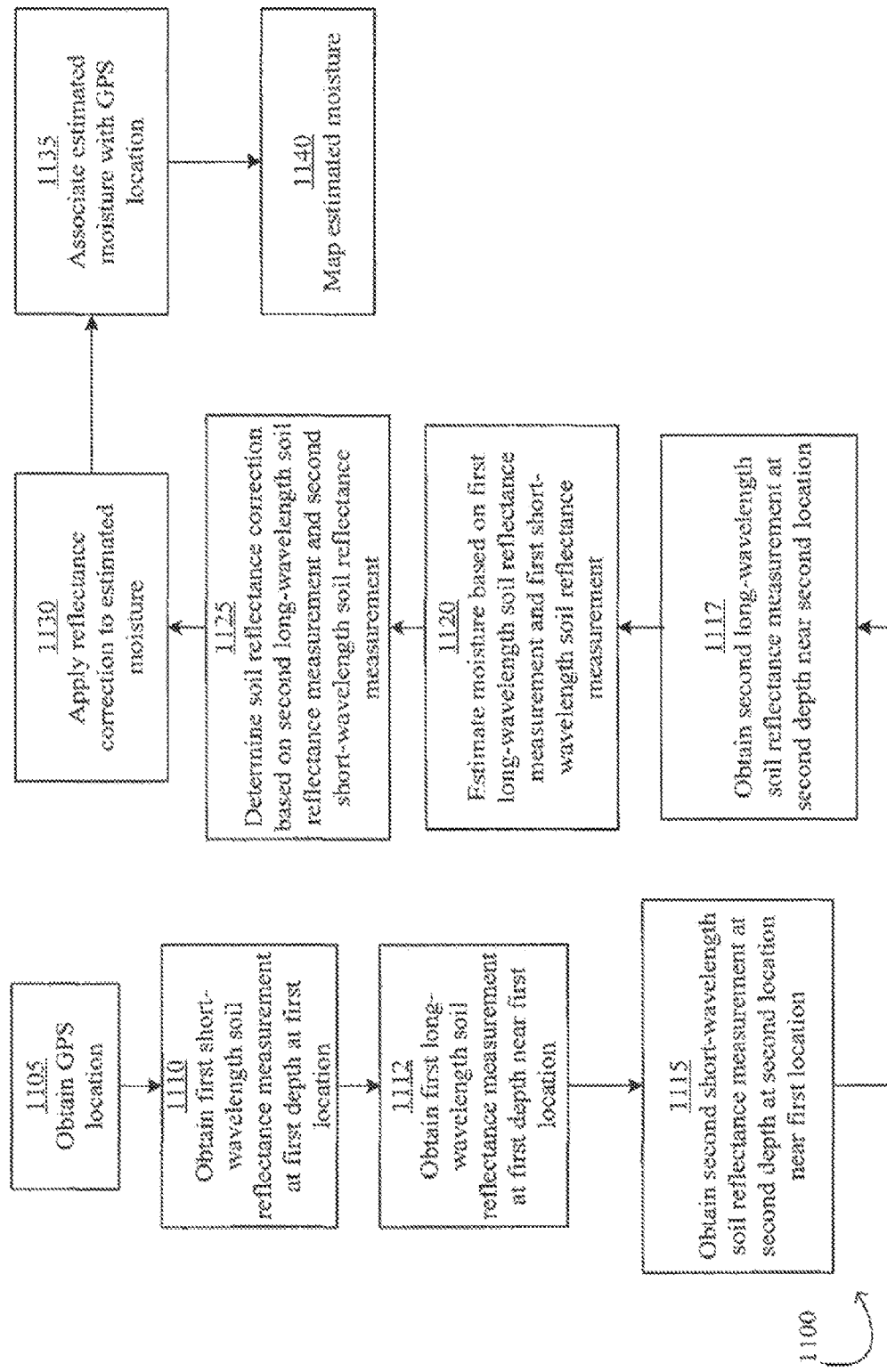
FIG. 11 illustrates an embodiment of a process for correcting a soil reflectance measurement made at multiple wavelengths using a second soil reflectance measurement made at multiple wavelengths.

Turning to FIG. 11, a process 1100 for correcting a moisture estimation based on reflectance measurements made at two wavelengths at a first depth during an in-field operation using a second reflectance-based moisture measurement made at a second depth is illustrated. At step 1105, the monitor 50 preferably determines the GPS location of the planter 10. At step 1110, the monitor 50 preferably obtains a first short-wavelength (e.g., between 380 nm and 750 nm) soil reflectance measurement near the obtained GPS location using the moisture sensor 350. At step 1112, the monitor 50 preferably obtains a first long-wavelength (e.g., between 750 nm and 3000 nm and preferably about 1600 nm) soil reflectance measurement near the obtained GPS location using the moisture sensor 350. The soil reflectance measurements made at step 1110 and step 1112 are made at a first depth; in some embodiments, the first depth is the same or approximately the same depth as the seed trench 38 opened by a row unit 16 of the planter 10.

Continuing to refer to FIG. 11, at step 1115, the monitor 50 preferably obtains a second short-wavelength (e.g., between 380 nm and 750 nm) soil reflectance measurement near the obtained GPS location using the moisture sensor 350. At step 1117, the monitor 50 preferably obtains a second long-wavelength (e.g., between 750 nm and 2000 nm and preferably about 1600 nm) soil reflectance measurement near the obtained GPS location using the moisture sensor 350. The soil reflectance measurements made at step 1115 and step 1117 are made at a second depth. In some embodiments the second depth is between 3 and 6 inches and preferably approximately 4 inches. In other embodiments, the second depth is between 0.5 inch and 1 inch and preferably approximately 0.75 inch. The second soil reflectance measurement is preferably made using a second-depth moisture sensor 352. In some embodiments, the second soil reflectance measurement is made using a second-depth moisture sensor mounted to the planter 10 such that the second soil reflectance measurement is made during the same in-field operation as the first soil reflectance measurement. In other embodiments, the second soil reflectance measurement is made during a prior in-field operation; for example, a second-depth moisture sensor 352 may be mounted to a toolbar used for soil tillage prior to planting.

Continuing to refer to FIG. 11, at step 1120 the monitor 50 preferably estimates a soil measurement (e.g., soil moisture) based on the first short-wavelength measurement and the first long-wavelength measurement. For a given mixture of soil and moisture, the total reflectance $R_T(\lambda)$ at a wavelength $\lambda$ may be related to the soil-based reflectance $R_s(\lambda)$ due to the soil components and the moisture-based reflectance $R_m(\lambda)$ due to moisture by the equation:

$$R_T(\lambda)=R_s(\lambda)+R_m(\lambda)+k_1$$

Where: $k_1$ is an empirically determined constant, e.g., 2%.

The first short-wavelength total reflectance measurement $R_T(\lambda_s)$ taken at step 1112 is preferably taken at relatively short wavelength $\lambda_s$ (e.g., 600 nm) for which the moisture-based reflectance $R_m(\lambda_s)$ is expected to be an empirically determined constant value $k_2$ (e.g., 10%) so that the soil-based reflectance $R_s(\lambda_L)$ may be determined by the equation:

$$R_s(\lambda_s)=R_T(\lambda_s)-k_1-k_2$$

The first high-wavelength total reflectance measurement $R_T(\lambda_l)$ taken at step 1112 is preferably taken at a wavelength $\lambda_l$ (e.g., 600 nm) at which the total reflectance $R_T$ correlates strongly (e.g., at an r-value greater than 0.8) with moisture and at which the expected value of $R_s(\lambda_l)$ may be estimated by the relationship:

$$R_s(\lambda_l)=k_3 R_s(\lambda_s)$$

Where: $k_3$ is an empirically determined factor, e.g., 1.2.

Thus, the value of $R_m(\lambda_l)$ may be estimated using the relationship:

$$R_m(\lambda_l)=R_T(\lambda_l)-k_3[R_T(\lambda_s)-k_1-k_2]$$

The monitor 50 preferably estimates the soil moisture M (in percent water weight) using the equation:

$$M=80-1.4R_m(\lambda_l)$$

Continuing to refer to FIG. 11, at step 1125 the monitor 50 preferably determines a soil reflectance measurement correction associated with the second soil reflectance measurements obtained at step 1115 and step 1117. In some embodiments, the monitor 50 first calculates a value of $R_{m2}(\lambda_l)$ calculated as the value $R_m(\lambda_l)$ was calculated above with respect to step 1125, but using the second-depth measurements taken at steps 1115 and 1117 rather than the first-depth measurements. A correction factor $k_4$ is calculated based on an expected value E (e.g., 15%) of $R_{m2}(\lambda_l)$ at the second depth using the equation:

$$k_4 = \frac{R_{m2}(\lambda_l)}{E}$$

The corrected moisture $M_c$ then calculated using the equation:

$$M_c=80-1.4k_4R_m(\lambda_l)$$

Continuing to refer to FIG. 11, at step 1130 the monitor 50 preferably applies the soil reflectance measurement correction obtained at step 1120 to estimated moisture, e.g., by adding the soil reflectance measurement correction to the estimated moisture. At step 1135, the monitor 50 preferably associates the estimated soil moisture with the GPS location, e.g., by storing the estimated soil measurement in a data array along with the GPS location. At step 1140, the monitor 50 preferably displays a map of the estimated soil measurement similar to that illustrated in FIG. 12.

Further Embodiments

In addition to reporting and mapping the moisture values measured as described herein, in some embodiments a trench depth is adjusted based on the moisture values as described in the '591 application, incorporated by reference above.

Where no wavelength or range of wavelengths is recited, the soil reflectance measurements taken herein may be taken using wavelengths in the visible (e.g., 380 nm to 750 nm), near-infrared ("NIR") (e.g., 750 nm to 1400 nm), or short-wavelength infrared (e.g., 1400 nm to 3000 nm) ranges. Additionally, the measurement may comprise a weighted sum or weighted average of reflectance values at multiple wavelengths. Where reflectance measurements are taken at two wavelengths at a single depth as recited herein, such measurements may be taken either by two similar devices disposed to measure reflectance at the same depth near the same location, or by rapidly changing the wavelength of light imposed by a single measurement device.

It should be appreciated that shifts and corrections applied herein to a reflectance value may instead be applied to the resulting estimated moisture value, and vice versa.

It should be appreciated that although actual moisture values calculated as described herein may not be equivalent to lab-tested values determined for a sample of the same soil, the spatial variance in moisture in the field will still provide accurate and important information to the operator in making tillage, crop input and planting depth decisions. Additionally, a confidence value may be associated with the calculated moisture values such that tillage, crop input, and depth adjustment decisions may be made based on a desired statistical confidence (e.g., 95%) that the soil moisture is greater than or less than a threshold value.

It should be appreciated that the systems and methods described herein may be implemented using other toolbars other than planter toolbars, e.g., tillage or side-dress toolbars.

The foregoing description is presented to enable one of ordinary skill in the art to make and use the invention and is provided in the context of a patent application and its requirements. Various modifications to the preferred embodiment of the apparatus, and the general principles and features of the system and methods described herein will be readily apparent to those of skill in the art. Thus, the present invention is not to be limited to the embodiments of the apparatus, system and methods described above and illustrated in the drawing figures, but is to be accorded the widest scope consistent with the spirit and scope of the appended claims.

The invention claimed is:

1. A method of measuring a soil characteristic during an operation in an agricultural field, comprising:
    making a first soil reflectance measurement at a location in the field;
    obtaining a second soil characteristic measurement, wherein said second soil characteristic measurement comprises a second soil reflectivity measurement at a different depth than said first soil reflectivity measurement;
    correcting said first soil reflectance measurement based on said second soil characteristic measurement; and
    estimating soil moisture at said location based on said corrected soil reflectance measurement.

2. The method of claim 1, wherein said second soil characteristic measurement comprises an electrical conductivity measurement.

3. The method of claim 1, wherein said second soil characteristic measurement comprises a pH measurement.

4. The method of claim 1, wherein said second soil characteristic measurement comprises a second soil reflectivity measurement at a different wavelength than said first soil reflectivity measurement.

5. The method of claim 1, further comprising:
    accessing a soil property map;
    determining a soil property at said location based on said soil property map; and
    correcting an estimated soil property based on said soil property.

6. The method of claim 5, wherein said soil property map comprises a soil type map.

7. A method of estimating soil moisture in a field, comprising:
    obtaining a first soil reflectance measurement at a first depth at a first location in the field;
    obtaining a second soil reflectance measurement at a second depth at a second location in the field;
    determining a reflectance-based reflectance correction based on said second soil reflectance measurement; and
    applying said reflectance-based reflectance correction to said first soil reflectance measurement to obtain a corrected first soil reflectance measurement; and
    estimating moisture using said corrected first soil reflectance measurement.

8. The method of claim 7, wherein said first soil reflectance measurement is carried out on a planter row unit, and wherein said second soil reflectance measurement is carried out on a separate row unit.

9. The method of claim 8, wherein said separate row unit opens a trench having a different depth than the planter row unit, and wherein said separate row unit includes a reflectance sensor for measuring reflectance of soil in said trench.

10. The method of claim 7, further comprising:
    associating said estimated moisture with said first location using a GPS receiver; and mapping said estimated moisture.

11. A method of estimating soil moisture in a field, comprising:
    obtaining a first soil reflectance measurement at a first wavelength at a first location;
    obtaining a second soil reflectance measurement at a second wavelength at a second location near said first location;
    obtaining a third soil reflectance measurement at said first wavelength at a third location near said first location, said third soil reflectance measurement being taken at a measurement depth, said measurement depth being different than said first soil reflectance measurement;
    obtaining a fourth soil reflectance measurement at said second wavelength at a fourth location near said first location, said fourth soil reflectance measurement being taken at said measurement depth; and
    estimating moisture based on said first soil reflectance measurement and said second soil reflectance measurement.

12. The method of claim 11, further comprising:
    determining a soil reflectance correction based on said third soil reflectance measurement and said fourth soil reflectance measurement; and applying said soil reflectance correction to said estimated moisture.

* * * * *